US007761382B2

(12) United States Patent
Becker et al.

(10) Patent No.: US 7,761,382 B2
(45) Date of Patent: Jul. 20, 2010

(54) METHOD AND SYSTEM TO PROTECT ELECTRONIC DATA OBJECTS FROM UNAUTHORIZED ACCESS

(75) Inventors: Detlef Becker, Möhrendorf (DE); Gerhard Mönnich, Erlangen (DE); Karlheinz Dorn, Kalchreuth (DE); Thomas Pohley, Erlangen (DE); Ivan Murphy, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 1252 days.

(21) Appl. No.: 10/800,351

(22) Filed: Mar. 12, 2004

(65) Prior Publication Data

US 2004/0210755 A1 Oct. 21, 2004

Related U.S. Application Data

(60) Provisional application No. 60/457,024, filed on Mar. 24, 2003.

(30) Foreign Application Priority Data

Mar. 14, 2003 (DE) ............................... 103 11 648

(51) Int. Cl.
*G06F 21/00* (2006.01)
(52) U.S. Cl. ................... 705/51; 705/2; 705/3; 705/59; 707/2; 707/10; 709/202; 725/29
(58) Field of Classification Search ................. 705/2–6, 705/51–58; 726/2–6; 709/202
See application file for complete search history.

(56) References Cited

U.S. PATENT DOCUMENTS 5,899,998 A * 5/1999 McGauley et al. ....... 707/104.1
5,924,074 A * 7/1999 Evans ............................ 705/3

| 6,345,461 | B1 | 2/2002 | Constant et al. |
| 6,347,329 | B1 * | 2/2002 | Evans .......................... 709/202 |
| 6,671,696 | B1 | 12/2003 | Holcombe et al. |
| 2002/0169781 | A1 | 11/2002 | Poole et al. |
| 2003/0050803 | A1 * | 3/2003 | Marchosky ..................... 705/3 |
| 2003/0065626 | A1 * | 4/2003 | Allen ........................... 705/76 |
| 2003/0088439 | A1 * | 5/2003 | Grushka ........................ 705/2 |
| 2003/0088440 | A1 * | 5/2003 | Dunn ............................ 705/3 |

(Continued)

FOREIGN PATENT DOCUMENTS

WO    WO 01/25882    4/2001

(Continued)

*Primary Examiner*—Pierre E. Elisca
*Assistant Examiner*—Shahid Kamal
(74) *Attorney, Agent, or Firm*—Schiff Hardin LLP (57) ABSTRACT

The invention concerns a method and a data processing system to protect an electronic data object from unauthorized access. Via a method, a) in a first step, an electronic data object identifier is generated dependent on the content of the data object, b) in a further step, an access right is determined dependent on the data object identifier, and c) in a last step, an access to the data object is allowed dependent of the access right. The data processing system comprises a data processing device and an access control module. Via the access control module, an electronic data object identifier can be generated dependent on the content of a data object, and an access right can be determined dependent on the data object identifier. The access right can comprises standard rights such as "Read" or "Write" and an "Execute" right to execute specific functionalities.

1 Claim, 3 Drawing Sheets

U.S. PATENT DOCUMENTS

| | | | |
|---|---|---|---|
| 2003/0101078 A1* | 5/2003 | Voegeli et al. | 705/2 |
| 2003/0140043 A1* | 7/2003 | Hotchkiss et al. | 707/10 |
| 2003/0191671 A1* | 10/2003 | Ulrich et al. | 705/2 |
| 2004/0034568 A1* | 2/2004 | Sone | 705/26 |
| 2006/0271493 A1* | 11/2006 | Stefik et al. | 705/59 |
| 2008/0059250 A1* | 3/2008 | Joao | 705/3 |
| 2009/0193451 A1* | 7/2009 | O'Neil | 725/29 |

FOREIGN PATENT DOCUMENTS

| | | |
|---|---|---|
| WO | WO 02/06750 | 1/2002 |
| WO | WO 03/017036 A2 | 2/2003 |

\* cited by examiner

METHOD AND SYSTEM TO PROTECT ELECTRONIC DATA OBJECTS FROM UNAUTHORIZED ACCESS

CROSS REFERENCE TO RELATED APPLICATIONS

The present application claims the benefit of U.S. Provisional Application No. 60/457,024, filed Mar. 24, 2003.

BACKGROUND OF THE INVENTION

The invention concerns a method to protect an electronic data object from unauthorized access, as well as a data processing system to execute the method and a storage medium on which is stored information to execute the method on a data processing device.

In increasing measure, the increased use of electronic data objects makes intelligent mechanisms for their protection from unauthorized access necessary. Data objects can be, for example, individual files, assembled file systems of file structures that serve for the storage or filing of information. The protection of data objects is particularly important in computer-aided workstations that are used by multiple persons and on which confidential information can be accessed. Such information occurs, among other things, in medical work environments, in laboratory, research, development environments or demographically-oriented work environments. Information referring to people must be protected in particular measure.

Protective mechanisms are known that are based on the encryption of the data objects. However, the encryption and decryption takes a relatively long time, particularly for large data objects, and is not practicable within work environments that are constrained to rationalized and economic functionalities. Moreover, the appropriate handling of sufficiently secure keys for encryption systems represents a considerable expenditure. Additionally, changes to the encryption system can only be implemented directly on the database itself, while the other copies of the data objects (for example, copies that are on data media or mobile workstations) are not reached.

Moreover, the protection of data objects based on the encryption offers no protection from the deletion of data objects and allows no differentiated allocation of access rights, for example, the differentiation between read, write or delete access. Furthermore, given asymmetric encryption methods, the entire receiver circle must already be known when encrypting since the public key of each receiver must be taken into account.

The protection of data objects on operating systems is also known in which the extent of the data access is provided determined by the rights of the user logged onto the operating system. The extent of the access rights is determined via an "Access Control List" (ACL) that is associated by the operating system with each data object in the file system. In the ACL of each data object, the user-dependent access rights are specifically listed for the respective operating system.

However, the ACL is part of the operating system or file system, and not of the data objects themselves, insofar as the ACL is merely copied when copying data objects within the file system (i.e., the ACL is handed down), while it is not preserved upon copying outside of the respective file system. This is not possible due to the operating system-specific functionality of the ACL. Moreover, changes to the access rights for data objects that are present in multiple copies within the file system can likewise not be centrally implemented since they are not automatically adopted by the copies of the data objects.

Moreover, it is advantageous, for example on medical systems in a clinical environment or on personnel or financial administration systems, to not limit specific functionalities only to specific users, but rather to introduce an additional dependency on the processed data. Thus, for example, in a clinical environment, all access rights to private patient data (with the exception of a read-right) could be unlocked exclusively for head doctors, while all doctors would have full access to the data of all other patients. Further differences could be implemented for data types such as laboratory reports (to which in principle only laboratory assistants must have editing access, while other clinical personnel only require read access). Similar differentiations are also likewise reasonably used in other work environments such as banks or personnel management.

A user typically receives (user-dependent and possibly system- or domain-dependent) a combination of "Create", "Read", "Update" and "Delete" rights, thus standard rights. Functional rights, thus designated as an "Execute" right, are exclusively assigned within an application and by the application itself, dependent on the data type or data content. An "Execute" right determines whether a specific functionality may be executed, such as, for example, an image processing event, the annotation of a data set, a finding in an electronic patient file, etc. The user-dependent assignment of standard rights is independent of the data-dependent assignment of functional "Execute" rights. The data-dependent assignment of "Execute" rights is in turn application-dependent and can therefore be handled differently in an undesired manner by different applications in different domains.

A particular problem of conventional mechanisms for access controls is represented by copies of data objects (for example, via sending by e-mail or via transfer to portable storage media) whose existence can be controlled/monitored neither in number nor in extent. Any possibility for subsequent, central change of access rights to copies belonging together with regard to content or analogous copies or modified copies is thereby made impossible. It is not to be effected on all data objects via the conventional control mechanisms since their number and whereabouts are unknown.

SUMMARY OF THE INVENTION

The object of the invention is to provide a method and a data processing system for allocation of access rights to electronic data objects created to store information that allows changes of the access rights for the data objects, including all copies thereof, from a central location.

The invention achieves this object via a method, via a data processing system, and via a storage medium with the respective features as follows. The invention provides a method to protect an electronic data object created to store information from unauthorized access, comprising: generating an electronic data object identifier dependent on content of the data object; determining an access right dependent on the data object identifier; and allowing an access of the data object dependent on the access right. The invention also provides a method to protect an electronic data object created to store information from unauthorized access, comprising: generating an electronic data object identifier as a copy of an identifier comprised in the data object utilizing information stored in the data object; determining an access right dependent on the data object identifier; determining an electronic user identifier of an operating personnel; determining the access right dependent on the user identifier; and allowing an access of the data object dependent on the access right. The invention also provides a method to protect an electronic data object created to store information from unauthorized access, comprising: generating an electronic data object identifier dependent on a content of the data object; determining an access right dependent on the data object identifier; and allowing an access of the data object dependent on the access right, the access right comprising a standard right and a functional right. The invention also provides a data processing system, comprising: a data processing device configured to access an electronic data object; and an access control module configured to a) generate an electronic data object identifier dependent on content of the data object, b) determine an access right dependent on the data object identifier, and c) allow access to the electronic data object dependent on the access right. Finally, the invention provides a data processing system, comprising: a data processing device configured to access an electronic data object; and an access control module configured to: a) generate an electronic data object identifier dependent on content of the data object; b) determine an access right comprising an access right and a functional right dependent on the data object identifier; and c) allow an access to the electronic data object dependent on the access right.

An important idea developed in embodiments of the invention is to provide a method to protect an electronic data object created to store information from unauthorized access, in that, in a first step, an electronic data object identifier is generated dependent on the content of the data object, in a further step an access right is determined dependent on the data object identifier, and in a last step an access to the data object is allowed dependent on the access right.

A data object should be understood to be a file as well as an object made from a plurality of files, or a file or index structure. An access right should be understood to be both standard rights and functional "Execute" rights. The standard rights are thus supplemented by freely definable access rights.

An important element of this fundamental thought is to use an electronic data object identifier dependent on the content of the data object. Access rights can thereby be determined from the data object itself. The content of the data object relevant for the determination of the access rights is likewise copied (thus handed down) upon copying since it belongs to the content, such that each copy of the data object also comprises the information necessary to determine the access rights.

The associations between access rights and data object identifiers on whose basis access rights are allowed can, for example, be stored in a table at a central location and changed such that changes to these associations are automatically valid for all copies of a data object. Access rights can thereby be changed at any time from the central location, independent of and even without the knowledge of the number and locations of copies. The access rights thereby comprise all standard rights and "Execute" rights for the data object.

A further important idea developed in embodiments of the invention is to provide a data processing system that comprises a data processing device via which an electronic data object created to store information can be accessed, and an access control module via which an electronic data object identifier can be generated dependent on the content of the data object, and via which an access right can be determined dependent on the data object identifier, and via which an access to the electronic data object can be allowed dependent on the access right.

The access control module enables access rights for the data object to be assigned dependent on information that is contained in the data object. Since the content of the data object is copied as well upon creation of copies, the allocation of access rights can therewith ensue uniformly from a central location for the data object as well as for all copies of it, and independent of the location of possible copies. "Access rights" should be understood to be all standard rights and "Execute" rights valid for the data object.

In an advantageous embodiment of the invention, the data object identifier is automatically generated using information stored in the data object. For example, the data object identifier can be assembled using a stored name and birth date and the content type, for example image or text. This allows the generation of data object identifiers that themselves carry information about the content of the data objects, such that the data objects could be systematically classified and arranged using the data object identifier. Such data identifiers can logically also be used for systematic allocation of access rights for classes of data objects when, for example, identical access rights should be assigned for all data objects of a specific relevance with regard to content, for example, for all laboratory reports, study results, diagnostic findings or billing data.

In a further advantageous embodiment of the invention, an electronic identifier is stored as such in the data object. It is then sufficient to generate the data object identifier in the data object as a copy of the identifier. In other words, the data object identifier then only has to be read out from the data object. The generation of the data object identifier as a direct copy of an identifier comprised in the data object also reduces the possibility for manipulation since no manipulatable steps are used for mediated, indirect generation of the data object identifier dependent on the content of the data object, for example, a composition of the data object identifier from a stored name and birth date.

A further advantageous embodiment of the invention is to execute the method on a data processing system that comprises an access right module via which data can be stored with regard to a mutual or reciprocal association of user identifiers and access rights, whereby the access control module of the data processing system determines an access right dependent on an access to the access right module.

"Module" is defined as any type of electronic service, for example, a server, an electronic library, or a process running on a computer. A modular arrangement of the access right module results within the data processing system that enables its central positioning at a flexible location. Changes to the allocation of access rights from a central location can thereby be effected. Via the access right module, the "Central Token Repository Module", access right categories are defined within which specific user identifiers are associated with specific access rights such as read, write, delete, copy or functional rights. The user identifiers thereby comprise both individual and group user identifiers.

A further advantageous embodiment of the invention exists in that the data processing system comprises a data object category module via which data can be stored with regard to a mutual association of data object identifiers and access right categories, and to which the access control module has access, whereby the access right is determined by the access control module dependent on an access to the data object category module. As above, a "module" is any electronic service, for example a server, an electronic library or a process running on a computer. The data object category module enables the establishment and changing of the association between data object identifier and access right category. Via changes within the data object category module, data object identifiers can be associated with other access right categories from a central location and the data access rights can thereby be changed.

Advantageously, all data objects and all copies thereof can be protected in a consistent manner. This means a user has identical access rights to each data object and each copy of it, independent of access location as well as of the storage location of the data object, insofar as it is located within the data processing system. This data processing system can be a network of a plurality of machines with flexible access possibilities. By suitably setting up the access rights, on can additionally ensure that data objects cannot leave this security domain.

An additional advantage is that the access rights of a user to a data object can be determined independent of the data object itself. Instead it is sufficient to know the data object identifier. This is possible without anything further in the event that the data object identifier is systematically generated from the content of the data object or further information concerning the data object. To determine the access rights for the appertaining data object, it is then sufficient to know the systematic information, for example, patient information and current station in a defined workflow. The access rights for data objects that can be associated with specific systematic categories can thus be determined independent of their location.

A further advantage is that data objects within the security domain can be transported independent of a data transport protocol or operating system. It is sufficient to merely maintain the integrity of a data object during the transport, such that the data object identifier necessary for determination of access rights can also be generated from copies of the data object.

The maintenance of the information to generate the data object identifier advantageously also enables the monitored transportation of the data object from one security domain to another security domain. Automatic changes of the access rights can thereby be achieved without something in the content of the data object having to be changed. This use of various security domains can particularly be used in workflow systems where, for example, data objects are transported from one department to another.

For example, it is thus possible in a clinical environment to allow different access rights for patient receiving, for radiology and for therapy, in that each of these work flow stages is represented by its own security domain. For this purpose, different access rights and data object categories are provided in different security domains. Domain-dependent, different access rights thereby result in a predetermined manner. Moreover, different user groups can also be provided as needed in order in particular to be able form different group affiliations.

A particular advantage may result in that the data object identifier can be generated dependent on content stored in a data object. The access rights can also be designed dependent on content. If the data objects undergo changes that, for example, can result in the execution of a task and storage of corresponding information in a data object, changed access rights can result in connection with this. For example, after adding confidential information regarding the person, a data object could be automatically barred from access for a specific class of personnel.

Further advantageous embodiments of the invention are described in more detail below.

DESCRIPTION OF THE DRAWINGS

Exemplary embodiments of the invention are subsequently explained in detail using the following Figures.

DETAILED DESCRIPTION OF THE PREFERRED EMBODIMENTS

Figure 1:
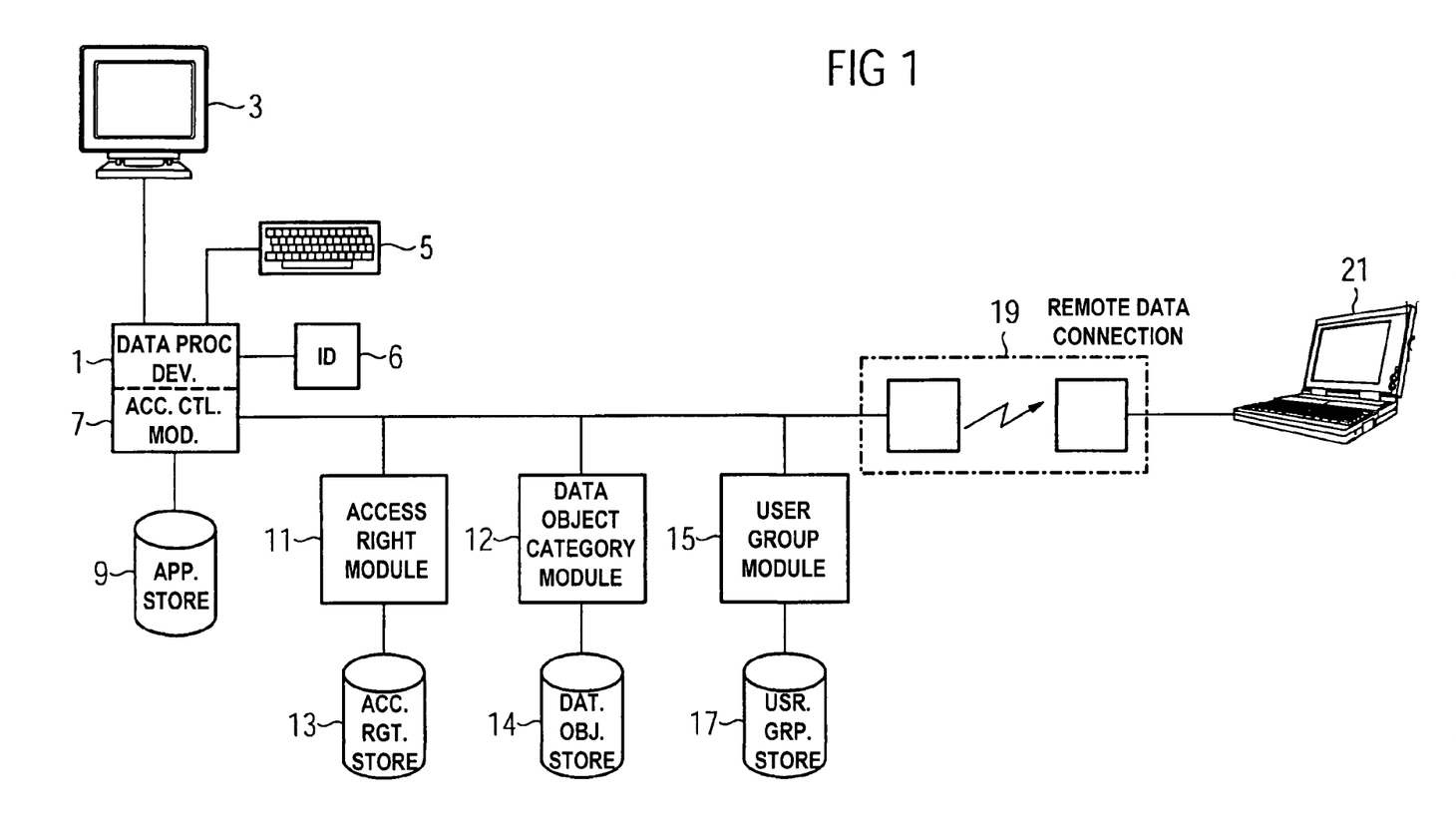
FIG. 1 is a block diagram of a data processing system to execute an embodiment the invention.

A data processing system to execute and embodiment of the invention is shown in FIG. 1. It comprises a data processing device 1 with a monitor 3 and a keyboard 5, via which electronic data objects can be accessed. The accessible data objects are located in an application storage 9. Accesses to data objects in the application storage 9 are monitored by the access control module 7.

The access control module 7 operates independent of access control mechanisms of the operating system such as, for example, a user-dependent, file specific ACL. In an advantageous embodiment, it is conceived as an additional program level (as a data access layer) and can be connected to the data bus of the data processing device 1 as a modular hardware component. However, its realization is also possible exclusively on a software level within the data processing device 1. The access control module 7 monitors all data accesses, for example deletions, copyings, creations, editings or execution of functionalities on those data objects that are subject to its control, meaning on all data objects within the security domain. In addition to this, it is naturally possible that other data objects (for example application programs or public, non-confidential data objects) are stored in the data storage 9 or, respectively, by the data processing device 1 independent of the access control module 7, thus outside of the security domain.

Upon starting the operating system of the data processing device 1, a user login is normally necessary in which a user must identify and authenticate himself for data accesses. The authentication comprises both the identification of a user and the authorization of the user for data accesses. To identify the user, a security query is provided in which, for example, a user identifier and a password must be input via the keyboard 5.

In this sense, any input mechanism can be understood as an identification mechanism 6. In a particularly advantageous embodiment, an identification mechanism implements an automatic query (for example, of a chip card, of a fingerprint, or of a shape of the iris) that enables the unambiguous identification of a user. The access control via the access control module 7 namely ensues independent of a user log in on the operating system, however it is also dependent on an identification of the user. For this, the same identification method via keyboard 5 or identification mechanism 6 can be used.

An important element for embodiments of the invention is that an unambiguous data object identifier can be generated for each electronic data object that is stored under access of the access control module 7. This can either be stored as such in the data object or it can be automatically generated from the content of the data object. For example, it can be the DICOM-UID appearing in DICOM data objects. The access control module 7 serves both to generate the identifiers that are then stored in a data object and to generate (or, said differently, extract) data object identifiers from the content of the data objects.

The data object identifier can be systematically assembled in order to be able to form structural connections such as workgroups, research teams, personnel hierarchies, contents referring to people, or contextual associations with subject areas or studies in the systems of the access rights. For example, the data object identifier in electronic patient files can comprise a data quadruplet identifying the patient, made up of patient name, gender, birth date and hospital identifier. This patient quadruplet is generally sufficient for unambiguous identification of a patient.

The data object identifier can also reflect the affiliation of the file with clinical studies, with series of diagnostic findings, or exposures over a longer period of time or with specific diagnostic image types such as x-ray exposure or ultrasound exposure. This structural information can be considered in the allowance of access rights such that individually different access rights are assigned, for example, for the treating doctor, for study attendants, for experts in radiology, or for accounting. By using this systematic information, an unambiguous data object identifier can be associated for each electronic data object, independent of the respective work environment.

To associate access rights using the specified systematic data object identifier, the access control module 7 requires information about the accessing user, his group affiliation, and about the association of data object types with specific access right categories. This information is respectively, specially filed and modularly accessible within the data processing system.

In a preferred embodiment, the system comprises an access right module 11 (for example, a server, a library or a process running on a computer) that has access to an access right storage 13 as well as to a user group module 15 (that likewise can be, for example, a server, a library or a process running on a computer) with access to a user group storage 17. Information for association of user identifiers with access right categories is stored in the access right storage 13. The access right categories respectively specify which user or user group is allowed to what extent for access rights. For example, an access right category can be defined as follows:

user A has no access
user B has read-only access
group C has full access
group D can execute functionalities 1 and 2
group E can execute functionality 2

The possible access rights comprise, for example, the creation of data objects, the creation of copies or handing down of information from data objects, the reading, changing and deletion of information that is stored in data objects, the changing of access rights within the respective access right category, and the execution of specific functionalities insofar as they are fundamentally available for execution on a workstation.

In the user group storage 17, information is stored that enables the association of a user identity or, respectively, user group dependent on the previously determined information for identification and authentication of the user. The user identity or user group is represented by an individual, electronic user identifier that enables an unambiguous identification within the data processing system. The group affiliation can, for example, reflect the affiliation with workgroups, with a function such as the on-duty senior physician, with a hierarchical categorization such as clinic director, with a professional orientation such as radiologist, or with a department affiliation such as personnel department or accounting.

The user identity and the group affiliation enable the structures of the work environment relevant for the determination of access rights to be completely formed. The association of a user with identities and groups can be centrally changed in the user group storage 17, and is therewith effective for any data access of the respective user in the entire system, independent of at which point in time or at which location the user wants to access data.

The access control module 7 associates electronic data objects using the electronic data object identifier of the access right categories in the access right storage 13. Using the electronic user identifier, accessing users are likewise associated with access right categories based on an access to the access right module 11. Via both of these associations, it can be determined which access right is allowed for which user upon access to a specific data object.

Via changes within the access control module 11 or within the user group module 15, the allowance of access rights can be changed from a central location for all data objects from which a specific data object identifier is generated, independent of the whereabouts of these data objects. Changes of these associations are also automatically effective for each copy of these data objects, since the part of their content from which the data object identifier is generated remains unchanged upon copying.

In a further preferred embodiment, the system comprises an access control module 11, a user group module 15, and additionally a data object category module 12 that can likewise be, for example, a server, a library or a process running on a computer. The data object category module 12 has access to a data object category storage 14 in which information is stored for association of data object identifiers and access right categories and can be changed.

In contrast to the preceding specification, this embodiment is more significantly modularized. As specified above, the user group module 15 provides information for determination of an electronic user identifier, and as before the access right module 11 provides information for association of user identifiers with access right categories. In addition to this, the data object category module 12 provides information that enables the association of data object identifiers with access right categories. Via the data object category module 12, it can be predetermined and changed for each data object which access right category it is associated with.

In each access right category, the users and user groups associated with this access right category then have the access rights predetermined therein. By changing an association in the data object category module 12, the access rights for a data object can thus be changed in adaptation to the cycling of a predetermined workflow in which different users or user groups should successively have access to the data object. In the clinical work environment, these stations could, for example, be the reception of the patients in the clinic, the entrance diagnosis, the subsequent examination by way of imaging radiology methods, the therapy, and the concluding diagnosis in which respectively different user groups (for example, medical-technical assistants, radiologists and therapists) work with the patient data objects.

When a data access should always ensue within the data processing system, thus within the security domain, the data object identifier of the data object to be accessed is first generated by the access control module 7. Via access to the user group module 15, the access control module 7 determines a user identifier and, using the user identifier, an access right category via access to the access right module 11. Via access to the data object category module 12, it determines (using the previously generated data object identifier) which access right category is associated with the data object. All information about the association of data object identifier and user identifier is therewith determined in order to be able to allow the user specific access rights to this data object.

The functionality of the access control module 7 can also be maintained for data accesses that ensue from remote workstations. For example, a mobile data processing device 21 (for example, a PDA or a notebook) can access data objects of the system via a remote data connection 19 (for example, a modem connection or a mobile radio connection). This can, for example, be the case given a home workstation or within a work environment such as a clinic given mobile devices.

The preceding specified design of the data processing system can be changed with regard to its modularity without changing the functionality of the access control module 7. For example, the user group storage 17 and the access right storage 13 can be unified on a common storage medium, or the access control module 11 and the user group module 15 can be integrated into a single data processing device. Their arrangement separate from the access control module 7 is also not necessary for the functionality, and they can instead be integrated into it. The modular design enables the particularly flexible use of the system for flexible allocation of access rights corresponding to all structural requirements of the respective work environment.

Figure 2:
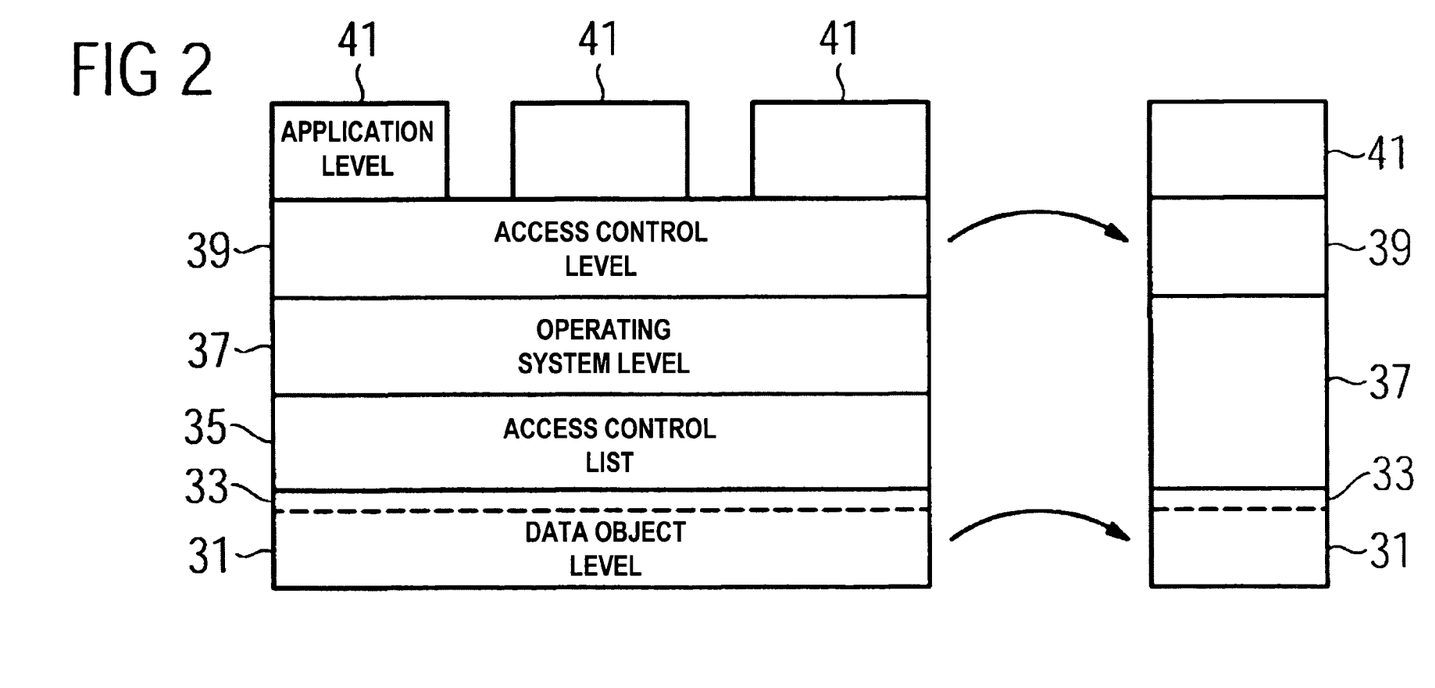
FIG. 2 is a block diagram showing a representation of logical levels within the data processing system.

In FIG. 2, logical levels are schematically shown within the data processing system, and thus within the security domain. Located on the lowest level 31 are the electronic data objects whose access is monitored. They comprise an identifier-relevant content 33 from which a data object identifier can be generated. This identifier-relevant content 33 must be arranged on a higher level, insofar as the data object identifier must be accessible independent of the access rights of a user in order to actually be able to first determine the extent of their access rights.

Above the data level, an ACL 35 can be arranged that monitors the access to the data on the level of the operating system and within the respective file system, dependent on the user login on the operating system. The ACL 35 is not part of the data object level 31, 33, insofar as it is not maintained upon exiting the respective file system or upon switching the operating system. It is not further handed down or transferred together with the data, but rather is lost. The ACL 35 is therefore shown as its own level in the schematic representation.

Above the ACL 35, the operating system level 37 is arranged that monitors the ACL 35 and moreover the data object level 31, 33.

The access control level 39, within which the function of the access control module 7 runs, sits on the operating system level 37. Via the operating system, it additionally monitors all data accesses to a potentially present access control.

The application level 41 with the application programs of the respective work environment is located above the access control level 39.

In the right part of the image, the logical levels are exemplarily shown that can result according to a transfer (graphically indicated by arrows) of files to a different operating system. The other operating system comprises no ACL in the selected example. The data object level 31, 33 is maintained unchanged, in particular the data object identifier 33 is transferred as well. However, due to the missing ACL, the access monitoring via the operating system level 37 is inapplicable.

However, the access to the data object level 31, 33 is also only possible via the access control level 39 after their porting. The monitoring of the access to the data in the considered extent is thus maintained even after its importation and independent of the change of the operating system. The application level 41 can furthermore exclusively access the data via the access control level 39.

Figure 3:
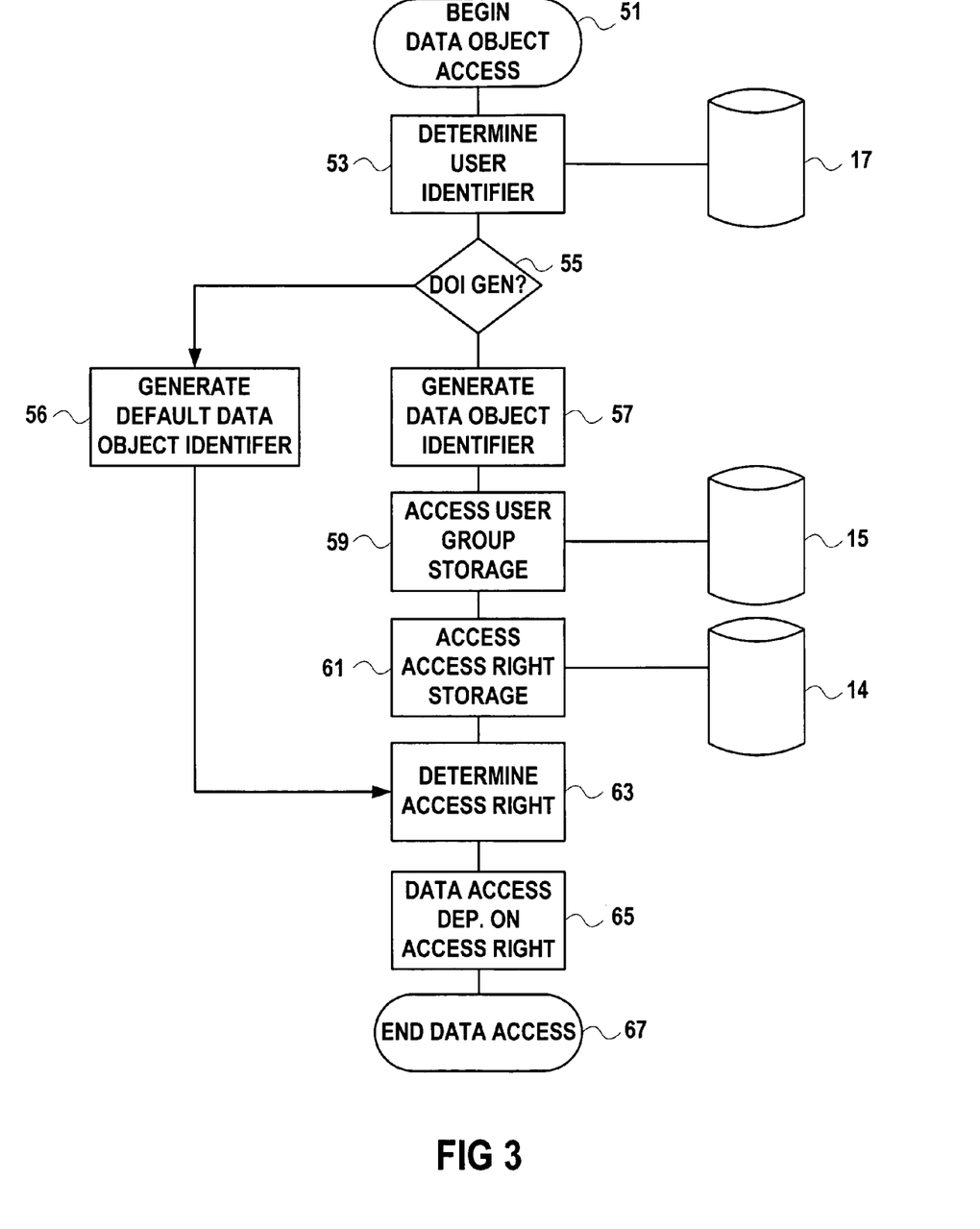
FIG. 3 is a flowchart showing method steps according to an embodiment of the invention.

The method steps upon access to data objects within the security domain are shown in FIG. 3. In step 51, the data object access begins from the side of a user or an application program.

In step 53, the determination of the user identifier ensues to identify the user. The information necessary for this can, as specified above, be acquired using keyboard inputs or biometric data acquisition. Using the data thus acquired, the user identifier is determined via access to the user group storage 17 via the user group module 15.

In step 55, it is tested whether the data object to be accessed enables the generation of a data object identifier. The data object identifier can either be specially stored in the data object or it can contain information that enables the automatic determination of an identifier.

If the generation of a data object identifier proves to be impossible, a default data object identifier is associated in step 56, via which a standard extent of access rights or default setting can be associated later. The access monitoring for data objects that, for example, have been introduced into the system without a data object identifier can thereby be realized by default and without the time-intensive implementation of further method steps to determine the access right extent.

If possible, in step 57 the data object identifier is automatically generated as a copy of an identifier stored in the data object or from content stored in the data object.

In step 59, the access control module 11 is accessed in order to determine an access right category using information of the access right storage 15. An association between user identifier and access right category (that, for example, can be stored as a table or as a map) is thereby queried.

In step 61, an access to the data object category module 12 ensues in order to obtain information from the data object category storage 14, via which an access right category associated with the previously determined data object identifier can be determined.

After all information for user identity, group identity and data object category are now present, in step 63 the access rights that are allowed for the user are determined. The determination ensues either on the basis of data queried in step 59 and step 61 or on the basis of standard values associated in step 56. The association of standard values can thereby ensue without further accesses to the modules, in order to prevent unnecessary accesses and save access times.

In step 65, the data access ensues and is allowed dependent on the previously determined access right.

The data access is ended in step 67. For example, the user can have logged out of the system, an automatic time-out from the system can ensue, or changes to the categories for determination of access rights can have been effected.

To illustrate program-technical aspects of the invention, some significantly simplified semantic instructions for method steps to realize the invention are subsequently reproduced. The simplifications include, for example, the omission of variable definitions and error handlings.

The user group module enables the creation, modification, deletion and querying of user and group identities. It comprises additional procedures for authentication of the respective user. The following instructions can be used for its realization:

```
bool createUser (wchar_t *theUserName, wchar_t *thePassword,
    wchar_t *&heSID);
bool deleteUser (wchar_t *theUserName);
bool querySID (wchar_t *theUserName, wchar_t *&theSID);
```

-continued

```
bool createGroup (wchar_t *theGroupName, wchar_t *&heGID);
bool deleteGroup (wchar_t *theGroupName);
bool queryGID (wchar_t *theGroupName, wchar_t *&theGID);
bool addUserToGroup (wchar_t *theSID, wchar_t *theGID);
bool removeUserFromGroup (wchar_t *theSID, wchar_t *theGID);
bool authenticateUser (wchar_t *theUserName, wchar_t
*theUserPassword, wchar_t *theUID);
bool releaseUID (wchar_t *theUID);
bool analyzeUID (wchar_t *theUID, wchar_t *&theSID, wchar_t
*&theGID);
```

"bool" is a C++ code word that can assume the Boolean values TRUE or FALSE and that stands before a variable definition, a method definition or a method declaration. "wchar_t" defines a Microsoft "wide" data type that may be, e.g., an unsighed short (16-bit) data object. "enum" is a C++ keyword that enables the definition of defined list types (enumerations). "struct" is a C++ keyword that enables the definition of new, assembled data types built from simpler data types.

The SID or GID are unambiguous identifiers for user or group identities and are used internally within the security domain. They serve to represent users and groups within the security domain without requiring that additional identities or names be used for them.

The other words of the instruction, for example createGroup or deleteGroup, are individually selected and are clear from their meanings.

A UID that unambiguously labels the user and the working session is generated with each successful authentication of a user. This UID is deleted as soon as the user logs off the system or the working session is ended by the security domain by a time-out.

The access right module can be realized using the following instructions:

```
Enum TokenRights
{
    Create,              // allow creation of new child objects in
hierarchical organized documents
    Read,                // allow reading contents of the document
    Update,              // allow modification of document contents
    Delete,              // allow deletion of complete document,
i.e. physical destruction
    Execute              // allow updating the current protections for
this document
    ExecuteSpecificFunction // allow executing of a spe-
cific function on contents of the document
};
bool createToken (wchar_t *theTokenName);
bool assignRight (wchar_t *theTokenName, wchar_t *theSID, To-
kenRights theGrantedRights);
bool assignRight (wchar_t *theTokenName, wchar_t *theGID, To-
kenRights theGrantedRights);
bool removeToken (wchar_t *theTokenName);
TokenRights authorize (wchar_t *theTokenName, wchar_t
*theSID, wchar_t *theGID);
```

The access right module 11 uses the SID and GID of a user in order to be able to determine his access rights. Group and user identities can be associated with different access rights and a user can assume a plurality of identities, such that all SIDs and GIDs must be evaluated in order to be able to determine the extent of the access rights of the respective user.

The association of data object identifiers with categories (that are designated as "Token" in the last instruction examples) allows the creation, deletion, searching and modification of the individual associations. They can be realized using the following instructions:

```
struct SecurityID    // sample definition for DICOM composite
documents
{
    wchar_t *thePatientQuadruple;
    wchar_t *theStudyInstanceUID;
};
bool setDefaultProtection(wchar_t *theTokenNames);
bool addProtection (SecurityID &theDocumentSecurityID,
wchar_t *theTokenNames);
bool queryProtection (SecurityID &theDocumentServiceID,
wchar_t *&theTokenNames);
bool removeProtection (SecurityID &theDocumentServiceID,
wchar_t *theTokenNames);
```

It is possible to associate a plurality of categories with a data object identifier. Data object identifiers that are associable with no category receive or are associated with a default extent of default access rights.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

Reference List 1 data processing device
3 monitor
5 keyboard
6 identification means
7 access control module
9 application storage
11 access right module
13 access right storage
14 data object category storage
15 user group module
17 user group storage
19 remote data connection
21 mobile data processing device
31 data object level
33 data object identifier level
35 access control list
37 operating system level
39 access control level
41 application level
51 begin data object access
53 determine user identifier
55 can the data object identifier be generated?
56 generate default data object identifier
57 generate data object identifier
59 access user group storage
61 access access right storage
62 access data object category storage
63 determine access right
65 data access dependent on access right
67 end data access

What is claimed is:

1. A method to protect from unauthorized access electronic data objects, each electronic data object being related to a particular medical patient, comprising the steps of:

providing a separate application data store containing said patient related electronic data objects, said data objects comprising in addition to a name of the respective patient one of the additional information types selected from a group consisting of at least laboratory reports, study results, diagnostic findings and billing data of the respective medical patient, each electronic data object having an associated data object identifier which is automatically generated using information stored in the data object so that the identifier is dependent on the content of the data object and wherein the data object identifiers themselves carry information in addition to said patient name about a content of the respective data objects comprising at least one of said additional information types selected from said group consisting of said laboratory reports, study results, diagnostic findings, and billing data of the respective medical patient so that the data objects are systematically classified and arranged for association with access right categories to form structural connections of the data object to groups, teams, or references to people;

providing a separate user group store for association of a plurality of unique medical field user IDs dependent on previously determined information for identification and authentication of the medical field users;

providing a separate data object category store for said association of said data object identifiers with said access right categories so that access rights can thereby be determined from the data object itself;

providing a separate access right store for associating said medical field user IDs with said access right categories so that it can be determined for a particular medical field user the type of access allowed for the particular medical field user for reading, changing, or deleting information contained in the data objects;

providing an access control module connected to access said access right store, said data object category store, and said user group store and which monitors and controls data accesses by said medical field users to said data objects in said data application store, said access control module determining a medical field user ID from the user group store, and using said medical field user ID, determining an access right category via said access right store, and via access to said data object category store, said access control module determining, using said data object identifiers, which access right category is associated with the data object which the medical field user is attempting to access.

* * * * *